United States Patent
Greszta-Franz et al.

(10) Patent No.: US 10,968,165 B2
(45) Date of Patent: Apr. 6, 2021

(54) POLYASPARTIC ACID ESTER COMPOSITIONS AND METHOD FOR PURIFICATION

(71) Applicant: Covestro Deutschland AG, Leverkusen (DE)

(72) Inventors: Dorota Greszta-Franz, Solingen (DE); Christian Drumm, Frohnhofen (DE); Jan Morbach, Cologne (DE); Reiner Witkowski, Bottrop (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/648,366

(22) PCT Filed: Sep. 14, 2018

(86) PCT No.: PCT/EP2018/074885
§ 371 (c)(1),
(2) Date: Mar. 18, 2020

(87) PCT Pub. No.: WO2019/057627
PCT Pub. Date: Mar. 28, 2019

(65) Prior Publication Data
US 2020/0223787 A1 Jul. 16, 2020

(30) Foreign Application Priority Data
Sep. 19, 2017 (EP) ................................ 17191793

(51) Int. Cl.
*C07C 227/40* (2006.01)
*C07C 229/24* (2006.01)
*C07C 227/06* (2006.01)

(52) U.S. Cl.
CPC .......... *C07C 227/40* (2013.01); *C07C 227/06* (2013.01); *C07C 229/24* (2013.01)

(58) Field of Classification Search
None
See application file for complete search history.

(56) References Cited

U.S. PATENT DOCUMENTS

| | | | |
|---|---|---|---|
| 5,126,170 A | 6/1992 | Zwiener et al. | |
| 5,214,086 A | 5/1993 | Mormile et al. | |
| 5,243,012 A | 9/1993 | Wicks et al. | |
| 5,364,955 A | 11/1994 | Zwiener et al. | |
| 5,412,056 A | 5/1995 | Zwiener et al. | |
| 5,559,204 A * | 9/1996 | Squiller ................ | C07C 251/08 528/60 |
| 5,623,045 A | 4/1997 | Zwiener et al. | |
| 5,821,326 A * | 10/1998 | Kurek ................... | C07C 227/18 528/332 |
| 6,458,293 B1 * | 10/2002 | Roesler ................. | C07C 229/24 252/182.23 |
| 6,590,066 B1 * | 7/2003 | Roesler .............. | C08G 73/1092 528/328 |
| 6,737,500 B1 * | 5/2004 | Roesler .............. | C08G 18/3821 528/328 |
| 6,790,925 B2 | 9/2004 | Danielmeier et al. | |
| 2002/0103326 A1 | 8/2002 | Primeaux, II et al. | |
| 2004/0063894 A1* | 4/2004 | Danielmeier ......... | C07C 229/24 528/44 |
| 2004/0067315 A1 | 4/2004 | Niesten | |
| 2007/0066786 A1 | 3/2007 | Hanson, Jr. et al. | |

FOREIGN PATENT DOCUMENTS

| | | | |
|---|---|---|---|
| CN | 107805207 | * | 3/2018 |
| DE | 19701835 A1 | | 7/1998 |
| DE | 102006002153 A1 | | 7/2007 |
| EP | 0667362 A1 | | 8/1995 |
| EP | 0816326 A1 | | 1/1998 |
| EP | 0893458 A1 | | 1/1999 |
| WO | WO 0107399 A1 | | 2/2001 |

OTHER PUBLICATIONS https://compass.astm.org/EDIT/htm_historical.cgi?D1209+00, downloaded on Sep. 22, 2020 (Year: 2020).*
International Search Report, PCT/EP2018/074885, dated Nov. 13, 2018, Authorized officer: Oliver Kleidemigg.
Houben Weyl, Meth. d. Org. Chemie vol. 11/1, 272 (1957).
Usp. Khim. 1969, 38, 1933.

* cited by examiner

*Primary Examiner* — Amy C Bonaparte
(74) *Attorney, Agent, or Firm* — Jed C. Benson

(57) ABSTRACT

The present invention relates to a method for purifying polyaspartic acid ester compositions and to the provision of polyaspartic acid ester compositions that contain 0.01 to <2% by weight fumaric acid dialkyl esters.

4 Claims, No Drawings

POLYASPARTIC ACID ESTER COMPOSITIONS AND METHOD FOR PURIFICATION

CROSS-REFERENCE TO RELATED APPLICATION

This application is a national stage application under 35 U.S.C. § 371 of PCT/EP2018/074885, filed Sep. 14, 2018, which claims the benefit of European Application No. 17191793, filed Sep. 19, 2017, each of which is incorporated herein by reference.

FIELD

The present invention relates to a process for purifying polyaspartic ester compositions and to the provision of polyaspartic esters containing 0.01% to <2% by weight of dialkyl fumarate.

BACKGROUND

Polyaspartic esters are used in two-component coating compositions that include a polyisocyanate component as a binder. Such coating compositions are suitable for the production of high-quality coatings that can be tailored to make them hard, elastic, and resistant to abrasion and solvents. An advantage over primary amines is the moderate reactivity of the amine functions present in the polyaspartic esters toward isocyanates.

EP0403921, EP0639628, EP0667362, EP0689881, U.S. Pat. Nos. 5,214,086, 6,605,684, EP0573860, EP0699696, EP0596360, EP0893458, DE19701835, DE102006002153, EP1767559, WO2001007504, WO2001007399, WO2004033517, U.S. Pat. No. 6,458,293, EP1426397, and U.S. Pat. No. 5,243,012 describe, by way of example, low-viscosity polyaspartic esters that have secondary amino groups and consequently show more moderate reactivity toward isocyanates compared to primary amines Such polyaspartic esters are also referred to as aspartates and are particularly suitable for the production of low-solvent or solvent-free coating compositions that show rapid hardening.

The synthesis of the polyaspartic esters is known per se and is carried out through addition of primary amines to an activated carbon-carbon double bond of vinylogous carbonyl compounds, as present for example in maleic or fumaric esters, which is adequately described in the literature (Hauben Weyl, Meth. d. Org. Chemie vol. 11/1, 272 (1957), Usp. Khim. 1969, 38, 1933).

In the reaction of maleic or fumaric esters with primary amines, the ratios of the reactants used are such that there is at least one, and preferably exactly one, olefinic double bond for every primary amino group. During production of a polyaspartic ester based on maleic or fumaric esters, an unwanted side reaction can occur in which dialkyl fumarate is formed as a minor component. A typical production process for a polyaspartic ester requires a storage time of 4-6 weeks once most of the starting materials have reacted with each other. During this time, the product undergoes so-called maturation, which is manifested by stabilization of the viscosity. Because conversion continues to increase during this time, the content of dialkyl fumarate falls too. This storage over several weeks results in significant logistics costs during production. Moreover, although the product is not shipped to the customer until the end of the storage period, it still contains substantial amounts of dialkyl fumarate, which can cause sensitization. On completion of the reaction, polyaspartic esters thus produced usually still contain residual amounts of 3 to 20% by weight of unreacted fumaric and/or maleic esters.

According to EP0403921, fumaric and/or maleic esters can be removed by distillation. The document does not specify the conditions under which removal can be successfully carried out. DE102006002153A1 likewise describes the production of aspartic esters in which diethyl fumarate is still present in a content of several percent by weight both in the crude product and after storage. Example 3 states that the excess diethyl fumarate was completely removed by thin-film distillation. Here too, there is no discussion of the required distillation conditions. Although this document describes the beneficial technical effects of a content of 2 to 10% by weight of diethyl fumarate in the aspartic ester, such as low viscosity allied with good pot life and final hardness, it should be pointed out here that a diethyl fumarate content this high also has the adverse effects already mentioned above.

SUMMARY

With these aspects in mind, it is desirable to provide polyaspartic esters containing less than 2% by weight of free dialkyl fumarates. A content of less than 0.01% by weight does not bring any further benefit in terms of processing conditions and is technically achievable only with considerable effort.

As already mentioned above, those skilled in the art are unable to establish from the prior art how a distillation needs to be conducted in order to obtain polyaspartic esters that have a low content of <2% by weight of diethyl fumarate. This is especially true if a light-colored product that can be used advantageously in coatings is to be obtained.

Arising from the above-described disadvantages, the object of the present invention is to provide a process for purifying polyaspartic ester compositions that provides polyaspartic esters which can be easily employed in the standard applications with minimal risk to health. This process is to be particularly suitable for polyaspartic esters that have a low platinum-cobalt color index.

This object has been achieved by the process according to the invention for purifying polyaspartic ester compositions to provide purified polyaspartic esters containing <2% by weight of dialkyl fumarate.

The present invention provides a process for purifying polyaspartic ester compositions comprising polyaspartic esters of the general formula (I)

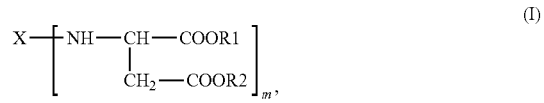

in which
X is an m-valent organic radical, optionally containing one or more heteroatoms, as can be obtained by removing primary amino groups from a corresponding polyamine that has aromatically, (cyclo)aliphatically or araliphatically attached primary amino groups and is in the molecular weight range from 60 to 6000 g/mol, and which may contain further functional groups that are reactive toward isocyanate groups and/or inert at temperatures of up to 100° C., R1 and R2 are identical or different organic radicals each having 1 to 18 carbon atoms, m is an integer >1, characterized in that the purified polyaspartic ester contains a proportion of 0.01% to <2% by weight of dialkyl fumarate.

DETAILED DESCRIPTION

The present invention preferably provides the above-mentioned process for purifying polyaspartic ester compositions of the general formula (I), in which X is an m-valent organic radical, optionally containing one or more heteroatoms, as obtained by removing primary amino groups from polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane, R1 and R2 are identical or different alkyl radicals each having 1 to 8 carbon atoms, m is an integer >1, characterized in that the purified polyaspartic ester contains a proportion of 0.01-0.2% by weight of dialkyl fumarate.

The present invention preferably further provides the above-mentioned process for purifying polyaspartic ester compositions comprising polyaspartic esters of the general formula (I), in which X is an m-valent organic radical as can be obtained by removing primary amino groups from 3,3'-dimethyl-4,4'-diaminodicyclohexylmethane, 2,4'- and/or 4,4'-diaminodicyclohexylmethane, 1,5-diamino-2-methylpentane, R1 and R2 are identical or different alkyl radicals selected from the group consisting of methyl, ethyl, propyl, isopropyl, butyl or isobutyl radicals, m is 2, characterized in that the purified polyaspartic ester contains a proportion of 0.01-0.2% by weight of dialkyl fumarate.

The present invention preferably further provides the above-mentioned process for purifying polyaspartic ester compositions comprising polyaspartic esters of the general formula (I), in which X is an m-valent organic radical as can be obtained by removing primary amino groups from 2,4'- and/or 4,4'-diaminodicyclohexylmethane, R1 and R2 are ethyl radicals, m is 2, characterized in that the purified polyaspartic ester contains a proportion of 0.01 to 0.1% by weight of dialkyl fumarate.

The present invention further provides a process for purifying polyaspartic ester compositions comprising polyaspartic esters of the general formula (I)

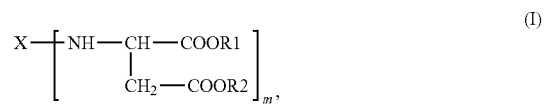

in which

X is an m-valent organic radical, optionally containing one or more heteroatoms, as obtained by removing primary amino groups from a corresponding polyamine that has aromatically, (cyclo)aliphatically or araliphatically attached primary amino groups and is in the molecular weight range from 60 to 6000 g/mol, and which may contain further functional groups that are reactive toward isocyanate groups and/or inert at temperatures of up to 100° C., R1 and R2 are identical or different organic radicals each having 1 to 18 carbon atoms, m is an integer >1 and preferably =2, characterized in that substituted maleic and/or fumaric esters of the general formula (II)

in which the radicals R1 and R2 have the meanings defined above, are reacted with primary polyamines of the general formula (III)

in which X and m have the meanings defined above, to form a polyaspartic ester composition comprising polyaspartic esters of the general formula (I) and purified in at least one further step, characterized in that the purified polyaspartic ester contains a proportion of 0.01% to <2% by weight of dialkyl fumarate.

The present invention preferably provides the above-mentioned process for purifying polyaspartic ester compositions of the general formula (I), in which X is an m-valent organic radical, optionally containing one or more heteroatoms, as obtained by removing primary amino groups from polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane, R1 and R2 are identical or different alkyl radicals each having 1 to 8 carbon atoms, m is an integer >1 and preferably =2, characterized in that substituted maleic and/or fumaric esters of the general formula (II), in which the radicals R1 and R2 have the meanings defined above, are reacted with primary polyamines of the general formula (III), in which X and m have the meaning defined above, to form a polyaspartic ester composition comprising polyaspartic esters of the general formula (I) and purified in a further step, characterized in that the purified polyaspartic ester contains a proportion of 0.01-0.2% by weight of dialkyl fumarate.

The present invention preferably further provides the above-mentioned process for purifying polyaspartic ester compositions comprising polyaspartic esters of the general formula (I),
in which
X is an m-valent organic radical as can be obtained by removing primary amino groups from 3,3'-dimethyl-4,4'-diaminodicyclohexylmethane, 2,4'- and/or 4,4'-diaminodicyclohexylmethane, 1,5-diamino-2-methylpentane,
R1 and R2 are identical or different alkyl radicals selected from the group consisting of methyl, ethyl, propyl, isopropyl, butyl or isobutyl radicals,
m is 2,
characterized in that substituted maleic and/or fumaric esters of the general formula (II), in which the radicals R1 and R2 have the meanings defined above,
are reacted with primary polyamines of the general formula (III), in which X and m have the meaning defined above,
to form a polyaspartic ester composition comprising polyaspartic esters of the general formula (I) and purified in a further step, characterized in that the purified polyaspartic ester contains a proportion of 0.01-0.2% by weight of dialkyl fumarate.

The present invention preferably further provides the above-mentioned process for purifying polyaspartic ester compositions comprising polyaspartic esters of the general formula (I),
in which
X is an m-valent organic radical as can be obtained by removing primary amino groups from 2,4'- and/or 4,4'-diaminodicyclohexylmethane,
R1 and R2 are ethyl radicals,
m is 2,
characterized in that substituted maleic and/or fumaric esters of the general formula (II), in which the radicals R1 and R2 have the meanings defined above,
are reacted with primary polyamines of the general formula (III), in which X and m have the meaning defined above,
to form a polyaspartic ester composition comprising polyaspartic esters of the general formula (I) and purified in a further step, characterized in that the purified polyaspartic ester contains a proportion of 0.01-0.1% by weight of dialkyl fumarate.

For the process according to the invention, preference is given to the use of dialkyl maleates and/or dialkyl fumarates of the formula (II), in which R1 and R2 are identical or different alkyl radicals each having 1 to 18 carbon atoms, preferably identical or different alkyl radicals each having 1 to 8 carbon atoms, and most preferably in each case alkyl radicals such as methyl, ethyl, propyl, isopropyl, butyl or isobutyl radicals. Particular preference is given to diethyl maleate. Examples of compounds of the general formula (II), which are not exhaustive, include the following diesters: dimethyl maleate, diethyl maleate, di-n-butyl maleate, the corresponding fumarates, or the corresponding maleates and fumarates having methyl substitution in the 2- and/or 3-position.

Polyamines of the general formula (III) that can be used for the process according to the invention are selected from the following group: all known polyamines having primary amino groups that conform to the general formula (III). Examples include the following compounds: ethylenediamine, 1,2-diaminopropane, 1,4-diaminobutane, 1,5-diaminopentane, 2,5-diamino-2,5-dimethylhexane, 1,5-diamino-2-methylpentane (Dytek® A, DuPont), 1,6-diaminohexane, 2,2,4- and/or 2,4,4-trimethyl-1,6-diaminohexane, 1,11-diaminoundecane, 1,12-diaminododecane or triaminononane, etheramines such as 4,9-dioxadodecane-1,12-diamine, 4,7,10-trioxatridecane-1,13-diamine, or higher-molecular-weight polyether polyamines having aliphatically attached primary amino groups, for example those marketed under the Jeffamine® name by Huntsman. Also employable are aliphatic polycyclic polyamines such as tricyclodecanebismethylamine (TCD diamine) or bis(aminomethyl)norbornanes, aminofunctional siloxanes, for example diaminopropylsiloxane G10 DAS (from Momentive), oleoalkyl-based amines, for example Fentamine from Solvay, dimeric fatty acid diamines such as Priamine from Croda.

In the process according to the invention, preference is given to the use of polyamines of the general formula (III) selected from the following group: polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane.

In the process according to the invention, particular preference is given to the use of polyamines of the general formula (III) selected from the following group: 3,3'-dimethyl-4,4'-diaminodicyclohexylmethane, 2,4'- and/or 4,4'-diaminodicyclohexylmethane, 1,5-diamino-2-methylpentane, and very particular preference to 2,4'- and/or 4,4'-diaminodicyclohexylmethane.

Also suitable are aromatic polyamines such as 2,4- and/or 2,6-diaminotoluene or 2,4'- and/or 4,4'-diaminodiphenylmethane or multiring homologs thereof. Further suitable are relatively high-molecular-weight polyether polyamines having aliphatically attached primary amino groups, for example those marketed under the Jeffamine® name.

Preferably, m is an integer >1 and is more preferably 2.

The polyaspartic ester composition comprising polyaspartic esters of the general formula (I) is produced by reacting the compounds of the general formula (II) and (III) at temperatures between 0° C. and 100° C., preferably 20 to 80° C., and more preferably 20 to 60° C., in a ratio of equivalents of primary amino groups in the compounds of the general formula (III) to C=C double bond equivalents in the compounds of the general formula (II) of 1:10, preferably 1:5, also preferably 1:2 and more preferably in a ratio of 1:1. The polyaspartic ester composition comprising polyaspartic esters of the general formula (I) can then be stored/matured for several weeks and/or processed for purification by the process according to the invention.

Polyaspartic ester compositions contain 70 to 98% by weight, preferably 80 to 98% by weight, and more preferably 85 to 98% by weight, of polyaspartic esters of the general formula (I).

In the context of the present invention, the purified polyaspartic ester is the product that is obtained by the process according to the invention for purifying polyaspartic ester compositions comprising polyaspartic esters of the general formula (I). It preferably contains a proportion of 0.01% to <2% by weight, preferably 0.01-0.2% by weight, and more preferably 0.01-0.1% by weight, of dialkyl fumarate.

For the purposes of the present invention, preference is given to purified polyaspartic esters having a platinum-cobalt color index of ≤100, preferably ≤50, and more preferably ≤30, and a proportion of 0.01% to <2% by weight, preferably 0.01-0.2% by weight, and more preferably 0.01-0.1% by weight, of dialkyl fumarate.

The present invention further provides the above-mentioned purification process, characterized in that polyaspartic ester compositions comprising polyaspartic esters of the general formula (I) having a platinum-cobalt color index of ≤100 are purified.

For maximum versatility when using the polyaspartic esters purified according to the invention in coatings, it is preferable if they have a platinum-cobalt color index of ≤100, more preferably ≤50. The platinum-cobalt color index is measured in accordance with DIN EN ISO 6271:2016-05. With the purification process according to the invention, it is surprisingly possible for discoloration of the polyaspartic esters of the general formula (I) to be largely avoided during purification. By contrast, lightening of already discolored polyaspartic ester compositions comprising polyaspartic esters of the general formula (I) is not to be expected, and so it is preferable if the process according to the invention is used for purifying polyaspartic ester compositions comprising polyaspartic esters of the general formula (I) that already have a platinum-cobalt color index of ≤100, more preferably ≤50, and particularly preferably ≤30.

The present invention further provides the above-mentioned purification process, wherein the polyaspartic ester compositions comprising polyaspartic esters of the general formula (I) are purified by distillation.

The present invention further provides the above-mentioned purification process, wherein the polyaspartic ester compositions comprising polyaspartic esters of the general formula (I) are purified by distillation at a pressure below 20 mbar and a temperature below 180° C.

The present invention further provides the above-mentioned purification process, wherein the polyaspartic ester compositions comprising polyaspartic esters of the general formula (I) are purified by distillation, characterized in that
 a) the distillation is carried out at a pressure between 0.005 and 2 mbar and
 b) the temperature of the bottom outflow on exiting the distillation apparatus is ≤170° C. and ≥the temperature resulting from formula (IV) below:

$$T(\text{bottom outflow}) = 27 \times \ln(p) + 150 \quad \text{(IV)},$$

where T(bottom outflow) is the temperature of the bottom outflow in ° C. and
p is the pressure in the distillation apparatus in mbar.

Preference is given to carrying out the distillation at a pressure between 0.005 and 2 mbar, preferably between 0.005 and 0.8 mbar, more preferably between 0.005 and 0.2 mbar.

Maintaining this pressure range ensures not only that moderate temperatures in the bottom outflow are sufficient for depletion of the dialkyl fumarate content to the desired degree, but that the process remains usable on an industrial scale. At lower pressure, the gas density becomes too low and the necessary equipment items consequently so large that the process becomes disadvantageous from an economic viewpoint.

The temperature of the bottom outflow is preferably ≤170° C., but at least 20 K above the temperature resulting from formula (IV); more preferably it is between 20 K and 40 K above the temperature resulting from formula (IV), but not above 170° C.

The present invention further provides the above-mentioned purification process, characterized in that the time during which the polyaspartic ester composition comprising polyaspartic esters of the general formula (I) is exposed to temperatures above 100° C. is less than 2 hours.

In a further preferred embodiment, the time during which the polyaspartic ester compositions comprising polyaspartic esters of the general formula (I) are exposed to temperatures above 100° C. is accordingly limited to less than 2 hours, preferably less than 30 minutes, more preferably less than 10 minutes. The higher the temperature, the shorter the chosen residence time at this temperature should be. This can be achieved for example by using distillation equipment and pipework of appropriate dimensions and has the advantage of minimizing the thermal stress of the material and associated discoloration.

Surprisingly, it has been found that a longer residence time at higher temperature results not only in an increase in the color index, but also in the retrocleavage of the polyaspartic ester. This retrocleavage results in the formation of new dialkyl fumarate. Attempts at further depleting the dialkyl fumarate content of the product down to the desired specification by the obvious option of increasing the temperature and/or residence time do not work. This is especially so after exiting the distillation apparatus, since any dialkyl fumarate that is subsequently formed will no longer be removed but instead remain in the purified product.

The present invention further provides the above-mentioned purification process, characterized in that the bottom outflow containing the purified polyaspartic ester is cooled to temperatures below 100° C. immediately after leaving the distillation apparatus.

The present invention further provides the above-mentioned purification process, characterized in that the bottom outflow containing the purified polyaspartic ester is cooled to temperatures below 100° C. immediately after leaving the distillation apparatus, wherein the mean residence time of the bottom outflow between exiting the distillation apparatus and entering a cooler is less than 5 minutes.

Preferably, the bottom outflow is accordingly cooled immediately after leaving the distillation apparatus to temperatures below 100° C., preferably below 80° C. In the present context, "immediately after leaving the distillation apparatus" is understood to mean that the mean residence time of the bottom outflow between exiting the distillation apparatus and entering a cooler is less than 5 minutes, preferably less than 2 minutes, and more preferably less than 1 minute.

In a multi-stage distillation, it is preferable if at least the final stage of the distillation is characterized by the conditions given above.

Examples of suitable apparatuses for the distillation according to the invention are falling-film evaporators, thin-film evaporators, and/or short-path evaporators. Preference is given to the use of thin-film evaporators and/or short-path evaporators, since these allow particularly gentle distillation.

The present invention further provides the above-mentioned purification process, characterized in that the distillation is carried out using falling-film evaporators, thin-film evaporators, and/or short-path evaporators.

The present invention further provides the above-mentioned purification process, characterized in that the distillation is carried out in two stages using a combination of a thin-film evaporator and subsequent short-path evaporator.

In a further preferred embodiment of the purification process according to the invention, the distillation is carried out in two stages, i.e. in two evaporators connected in series, wherein the purified polyaspartic ester is in each case obtained in the evaporator bottoms. For conformance with the pressure conditions for the purification process according to the invention on an industrially relevant scale too, it is particularly preferable to select a combination of a thin-film evaporator and subsequent short-path evaporator. Such an arrangement allows pressure drops to be minimized and the polyaspartic ester to be distilled in the second stage at particularly low pressure, for example between 0.005 and 0.2 mbar, and thus gently at low temperatures too.

The present invention further provides polyaspartic ester compositions comprising compounds of the general formula (I)

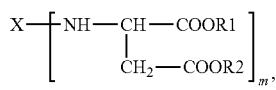

in which
- X is an m-valent organic radical, optionally containing one or more heteroatoms, as obtained by removing primary amino groups from a corresponding polyamine that has aromatically, (cyclo)aliphatically or araliphatically attached primary amino groups and is in the molecular weight range from 60 to 6000 g/mol, and which may contain further functional groups that are reactive toward isocyanate groups and/or inert at temperatures of up to 100° C.,
- R1 and R2 are identical or different organic radicals each having 1 to 18 carbon atoms,
- m is an integer >1 and preferably =2, characterized in that a proportion of 0.01% to <2% by weight of dialkyl fumarate is present and the platinum-cobalt color index is <100.

The present invention further provides polyaspartic ester compositions comprising compounds of the general formula (I), in which
- X is an m-valent organic radical, optionally containing one or more heteroatoms, as obtained by removing primary amino groups from polyether polyamines having aliphatically attached primary amino groups, 1,2-diaminopropane, 1,4-diaminobutane, 1,5-diaminopentane, 1,6-diaminohexane, 1,5-diamino-2-methylpentane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane or 3,3'-dimethyl-4,4'-diaminodicyclohexylmethane,
- R1 and R2 are identical or different alkyl radicals each having 1 to 8 carbon atoms,
- m is an integer >1 and preferably =2, characterized in that a proportion of 0.01-0.2% by weight of dialkyl fumarate is present and the platinum-cobalt color index is <50.

The present invention further provides polyaspartic ester compositions comprising compounds of the general formula (I), in which
- X is an m-valent organic radical as can be obtained by removing primary amino groups from 3,3'-dimethyl-4,4'-diaminodicyclohexylmethane, 2,4'- and/or 4,4'-diaminodicyclohexylmethane, 1,5-diamino-2-methylpentane,
- R1 and R2 are identical or different alkyl radicals selected from the group consisting of methyl, ethyl, propyl, isopropyl, butyl or isobutyl radicals,
- m is 2, characterized in that a proportion of 0.01-0.2% by weight of dialkyl fumarate is present and the platinum-cobalt color index is <30.

The present invention further provides polyaspartic ester compositions comprising compounds of the general formula (I), in which
- X is an m-valent organic radical as can be obtained by removing primary amino groups from 2,4'- and/or 4,4'-diaminodicyclohexylmethane,
- R1 and R2 are ethyl radicals,
- m is 2, characterized in that a proportion of 0.01-0.1% by weight of dialkyl fumarate is present and the platinum-cobalt color index is <30.

EXPERIMENTAL

The invention is elucidated hereinafter with reference to examples.

The starting substance used was tetraethyl N,N'-(methylenedicyclohexane-4,1-diyl)bis-DL-aspartate (CAS No. 136210-30-5) that had a platinum-cobalt color index of 15 and a diethyl fumarate content of approx. 5% by weight. This is referred to hereinafter as polyaspartic ester A.

The content of diethyl fumarate in the samples was quantified by means of a GC method with internal standard. An Agilent GC with a fused silica capillary and FID detector was used. The injector temperature (split outlet) was 180° C. and helium was used as the carrier gas. The quantitation limit of this method was 300 ppm.

Example 1

Polyaspartic ester A was first purified by distillation to a dialkyl fumarate (DF) content in the purified polyaspartic ester of 0.07% by weight. Samples of this purified polyaspartic ester were then subjected to heat treatment at 70° C., 100° C., and 130° C. The heat-treated samples were analysed for their DF content at the start and after 2 h and 5 h, The results for the heat treatment are summarized in table 1 below. The percentages shown are each percentages by weight of DF in the sample.

TABLE 1

| Temperature | Starting value | Heating for 2 h | Heating for 5 h |
| --- | --- | --- | --- |
| 70° C. | 0.070% | 0.065% | 0.075% |
| 100° C. | 0.050% | 0.095% | 0.150% |
| 130° C. | 0.070% | 0.260% | 0.75% |

Example 2

200 kg of polyaspartic ester A is distilled at 0.25 mbar in a thin-film evaporator. The temperature of the bottom outflow here is 140° C. and the mean residence time of the product in the evaporator is approx. 5 minutes. The distilled product is collected in a steel container, without undergoing an additional cooling step, and stored temporarily therein. The product cools down slowly during this operation. After 2 hours the temperature falls to below 100° C. A sample is collected and analysed for its DF content. This is 0.22% by weight and the platinum-cobalt color index of the sample is 33.

Example 3

200 kg of polyaspartic ester A is distilled as described in example 2. However, immediately after leaving the evaporator, the bottom outflow is then fed into a heat exchanger, where it is cooled to 70° C. prior to transfer of the product to a steel container for storage. After 2 hours, a sample is collected and analysed for its DF content. This is 0.07% by weight and the platinum-cobalt color index of the sample is 30.

Example 4

200 kg of polyaspartic ester A is distilled as described in example 3, with the difference that this time the pressure is set at 1 mbar. A sample of the stored product is collected after 2 hours and analysed for its DF content. This is 0.7% by weight and the platinum-cobalt color index of the sample is 28.

Example 5

200 kg of polyaspartic ester A is distilled as described in example 2, i.e. without rapid cooling of the bottom outflow. In a departure from example 2, the pressure this time is set at 0.5 mbar and the heating power is increased so that the temperature of the bottom outflow is 175° C. The sample after 2 h has a DF content of 0.37% by weight. The product also shows discoloration. The platinum-cobalt color index is 240.

The invention claimed is:

1. A polyaspartic ester composition, comprising: a compound of the general formula (I)

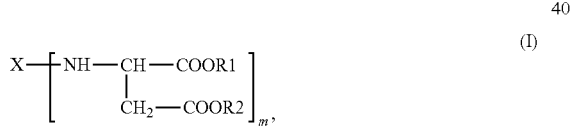

in which
X is an m-valent organic radical obtained by removing primary amino groups from a corresponding polyamine in the molecular weight range from 60 to 6000 g/mol, and which comprises further functional groups that are reactive toward isocyanate groups and/or inert at temperatures of up to 100° C., wherein the m-valent organic radical optionally contains one or more heteroatoms, and wherein the corresponding polyamine comprises aromatically, (cyclo)aliphatically, or araliphatically attached primary amino groups,
R1 and R2 are identical or different organic radicals each having 1 to 18 carbon atoms,
m is an integer >1
wherein the polyaspartic ester composition comprises from 0.01% to <2% by weight of dialkyl fumarate and has a platinum-cobalt color index of <100.

2. A process for purifying a polyaspartic ester composition comprising: forming a polyaspartic ester of the general formula (I)

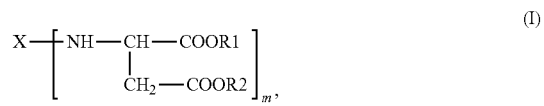

in which
X is an m-valent organic radical obtained by removing primary amino groups from a corresponding polyamine in the molecular weight range from 60 to 6000 g/mol, and which comprises further functional groups that are reactive toward isocyanate groups and/or inert at temperatures of up to 100° C., wherein the m-valent organic radical optionally contains one or more heteroatoms, and wherein the corresponding polyamine comprises aromatically, (cyclo)aliphatically, or araliphatically attached primary amino groups,
R1 and R2 are identical or different organic radicals each having 1 to 18 carbon atoms,
m is an integer >1,
by combining substituted maleic or fumaric esters of the general formula (II)

R1OOC—CH=CH—COOR2    (II), with primary polyamines of the general formula (III)

X—(—NH$_2$)$_m$    (III), to form the polyaspartic ester of the general formula (I); and
purifying the polyaspartic acid ester to form the polyaspartic ester composition of claim 1, wherein purifying comprises distillation that is carried out at a pressure below 20 mbar and a temperature below 180° C. using a distillation apparatus selected from a falling-film evaporator, a thin-film evaporator, a short-path evaporator, or a combination thereof and further comprises cooling a bottom outflow containing a purified polyaspartic ester to a temperature below 100° C. immediately after leaving the distillation apparatus.

3. The process as claimed in claim 2, wherein
a) distillation is carried out at a pressure between 0.005 and 2 mbar and
b) a temperature of the bottom outflow upon exiting the distillation apparatus is ≤170° C. and ≤a temperature resulting from formula (IV) below:

$T(\text{bottom outflow})=27\times\ln(p)+150$    (IV), where T(bottom outflow) is the temperature of the bottom outflow in ° C. and
p is a pressure in the distillation apparatus in mbar.

4. The process as claimed in claim 2, wherein distillation is carried out in two stages using a combination of a thin-film evaporator and subsequent short-path evaporator.

* * * * *